United States Patent [19]
Smith et al.

[11] Patent Number: 4,989,609
[45] Date of Patent: Feb. 5, 1991

[54] DOPPLER BLOOD FLOW SYSTEM AND METHOD USING SPECIAL ZERO FLOW RATE ANALYSIS

[75] Inventors: Dirk R. Smith, St. Paul; Billy L. Weaver, Eagan, both of Minn.

[73] Assignee: Minnesota Mining and Manufacturing Company, St. Paul, Minn.

[21] Appl. No.: 302,402

[22] Filed: Jan. 26, 1989

[51] Int. Cl.$^5$ ............................................. A61B 5/026
[52] U.S. Cl. .............................. 128/661.08; 73/861.25
[58] Field of Search ....................... 128/661.07, 661.08, 128/661.09, 661.1, 662.04, 663.01; 73/631, 861.25; 604/65

[56] References Cited

U.S. PATENT DOCUMENTS

| | | | |
|---|---|---|---|
| 3,498,290 | 3/1970 | Shaw et al. | 73/861.25 |
| 4,690,002 | 9/1987 | Hubbard | 73/861.25 |
| 4,743,228 | 5/1988 | Butterfield | 604/65 |
| 4,807,636 | 2/1989 | Skidmore et al. | 73/861.25 |

OTHER PUBLICATIONS

Atkinson, Peter et al, "A Fundamental Interpretation of Ultrasonic Doppler Velocimeters", Ultrasound in Medicine & Biology, vol. 2, pp. 107-111, Pergamon Press (1976).
Newhouse, et al, "The Effects of Geometric Spectrum Broadening On Ultrasonic Doppler Flow Measurement Systems", *29th ACEMB Proceedings*, p. 140 (1976).
Lunt, M. J., "Accuracy and Limitations of the Ultrasonic Doppler Blood Velocimeter and Zero Crossing Detector", *Ultrasound in Medicine and Biology*, vol. 2, pp. 1-10.
Brody, "Theoretical Analysis of the CW Doppler Ultrasonic Flowmeter", *IEEE Transactions on Biomedical Engineering*, vol. BME-2, No. 3, pp. 183-192 (1974).
Sears et al, *College Physics*, Fourth Edition, pp. 366-367, Addison-Wesley Publishing Company (1974).
Atkinson & Woodcock, *Doppler Ultrasound and its Use in Clinical Measurement*, Chapters 1 and 3, Academic Press (1982).
Murphy and Rolfe, "Application of the TMS320 Signal Processor for the Real-Time Processing of the Doppler Ultrasound Signal", *IEEE/Eighth Annual Conference of the Engineering in Medicine and Biology Society*, pp. 1175-1178 (1986).

Primary Examiner—Kyle L. Howell
Assistant Examiner—Krista M. Pfaffle
Attorney, Agent, or Firm—Donald M. Sell; Walter N. Kirn; William D. Bauer

[57] ABSTRACT

A Doppler blood flow system and method in which an ultrasonic wave is reflected off of red blood cells in blood flowing in tubing. The reflected ultrasonic wave is digitally processed in the frequency domain. The flow rate of the blood is directly related to the average frequency of the Doppler signal. Because the Doppler blood flow system calculates flow rate solely on the basis of frequency, a special case exists at zero rate of flow where the received signal is not a valid Doppler flow signal, but rather purely noise. The noise at zero flow rate is random and will not have an average frequency which is unique to zero flow. The Doppler blood flow system and method must invoke a special case determination of when a zero flow condition exists in order to accurately provide a blood flow rate. The system utilizes a method of determining the rate of flow of a fluid containing particles flowing through a tube. An ultrasonic signal is transmitted through the tube at an oblique angle thereto. The ultrasonic signal which has been reflected off of the particles contained in the fluid is received as a received ultrasonic signal. The rate of flow of the fluid is calculated from the received ultrasonic signal using Doppler techniques. Whether the special case of the value of the rate of flow being equal to zero exists is determined and the value of the rate of flow is set equal to zero for the special case.

4 Claims, 5 Drawing Sheets

DOPPLER BLOOD FLOW SYSTEM AND METHOD USING SPECIAL ZERO FLOW RATE ANALYSIS

BACKGROUND OF THE INVENTION

The present invention relates generally to Doppler blood flow measurement systems and techniques, and more particularly to Doppler blood flow measurement systems and techniques using the frequency domain signal analysis.

During cardiopulmonary bypass surgery, ventricular assist using blood pumps and other cardiac surgeries, blood flow external to the patient is necessary. Known blood pumps and so-called heart-lung machines operate to transport the blood of the patient through tubing or conduits in order to perform their function. During the transportation of blood in these external (to the body of the patient) tubes or conduits, it is extremely important for the surgeon to monitor the rate of flow of the blood so that abnormalities in the flow can be detected and corrective action can be taken.

Various systems and techniques have been utilized to measure the flow of blood, or other fluids, through tubes or conduits in the past.

Invasive measurement systems including techniques such as vane type flow meters not only require either disposal or sterilization after each use, but, with blood, may lead to unwanted coagulation or other problems. U.S. patent application Ser. No. 07/074,549, Lloyd C. Hubbard and Earl W. Clausen, filed July 17, 1987, entitled FLOW MEASUREMENT SYSTEM, assigned to Minnesota Mining and Manufacturing Company who is the assignee of the present invention, describes a blood flow measurement system for use with a motor driven centrifugal pump. The system takes advantage of the fact that, at a constant speed of rotation and a constant viscosity, the torque required to drive a centrifugal pump is directly related to the flow produced by the pump. Blood flow is computed from the speed of rotation of the pump and the torque of the motor.

The use of ultrasound to determine the flow of blood in a blood vessel started generally in the 1950's. Some of these ultrasound systems were implanted into the patient and some utilized measurements taken external to the patient.

The ultrasonic measurement of blood flow through tubes or conduits using the known Doppler frequency shift effect has been utilized. Such a measurement system and technique has the distinct advantage of being non-invasive. The tube or conduit, being relatively transparent to the ultrasonic waves, need not be physically invaded. In such known systems and techniques an ultrasonic transmitter is placed angularly with respect to the expected blood flow through the tube or conduit. An ultrasonic receiver is angularly placed on the opposite or same side of the tube or conduit. The presence of particulates, such as red blood cells, air bubbles and fat globules, act as targets for the reflection of the ultrasonic signal. The velocity of these targets cause a frequency shift in the reflected ultrasonic frequency according to the well known Doppler effect.

An example is a prior flowmeter marketed by Sarns, Inc. of Ann Arbor, Mich. (now a subsidiary of Minnesota Mining and Manufacturing Company, St. Paul, Minn., the assignee of the present application) known as the Sarns model 7800 flowmeter. An accuracy of about ± ten percent (10%) was achievable with this device. Indeed, in order to achieve this accuracy the console of each flowmeter must be matched to an individual flowprobe at the time of manufacture. Due to the matching requirement, manufacturing and field service was made more difficult and interchangeability of probes between flowmeters could not be achieved.

The system described in U.S. Pat. No. 4,690,002, Hubbard et al, also assigned to Minnesota Mining and Manufacturing Company, is an example of an ultrasonic Doppler blood flow measurement system. This system operates on an analog basis by amplifying the reflected signal, clipping it, using automatic gain control to restrain the signal into a reasonably finite range and converting the signal from a frequency to a voltage by use of an analog frequency-to-voltage converter.

In Atkinson, Peter, "A Fundamental Interpretation of Ultrasonic Doppler Velocimeters", *Ultrasound in Medicine & Biology*, Volume 2, pp. 107-111, Pergamon Press (1976), a description is provided for basic Doppler velocimeters and their usefulness in medical and industrial fields. Atkinson notes that in useful Doppler systems, as opposed to theoretical systems, that the received signal will exhibit a range of Doppler difference spectrum rather than a single frequency predicted by a perfect system. This range of spectrum will be exhibited by a "hump" or bell-shaped curve in the frequency domain. The cause may be the propagation of a finite width beam as opposed to an arbitrarily narrow pulse or may be caused by a finite length of pulse in a pulsed system as opposed to an infinitely short pulse. Atkinson also discloses that the reflection (backscatter) from blood will be amplitude modulated due to differences in time of the volume of red blood corpuscles.

An article by Newhouse et al, "The Effects of Geometric Spectrum Broadening On Ultrasonic Doppler Flow Measurement Systems", *29th ACEMB Proceedings*, p. 140 (1976) discusses that spectrum broadening in ultrasonic Doppler flow systems is due to geometric broadening.

An article by Lunt, M. J., "Accuracy and Limitations of the Ultrasonic Doppler Blood Velocimeter and Zero Crossing Detector", *Ultrasound in Medicine and Biology*, Volume 2, pp. 1-10 (1975), discusses the use of zero crossing detectors in ultrasonic Doppler blood flow measurement.

An article by Brody, "Theoretical Analysis of the CW Doppler Ultrasonic Flowmeter", *IEEE Transactions on Biomedical Engineering*, Volume BME-2, No. 3, pp. 183-192 (1974) discusses the theoretical basis for ultrasonic continuous wave Doppler blood flowmeters.

A portion of a Chapter from Sears et al, *College Physics*, Fourth Edition, pp. 366-367, Addison-Wesley Publishing Company (1974) describes the basic Doppler effect as related to acoustic phenomenon.

A book by Atkinson & Woodcock, *Doppler Ultrasound and its Use in Clinical Measurement*, Chapters 1 and 3, Academic Press (1982) provides an introduction into Doppler sound wave theory and its reaction to the measurement of blood and exemplary systems for the processing and analysis of Doppler shift signals. This books provides a good discussion of the conversion of the Doppler from the time domain to the frequency domain.

An article by Murphy and Rolfe, "Application of the TMS320 Signal Processor for the Real-Time Processing of the Doppler Ultrasound Signal", *IEEE/Eighth Annual Conference of the Engineering in Medicine and Biol-* ogy Society, pp. 1175–1178 (1986) describes techniques to achieve real-time processing of Doppler ultrasound signals applied to the measurement of blood flow. Murphy et al uses Fast Fourier Transform (FFT) techniques to convert from the time domain to the frequency domain and to digitally obtain the average frequency which corresponds to the blood flow measured.

SUMMARY OF THE INVENTION

Because the flowmeter of the present invention and the method invoked therein calculates flow rate solely on the basis of frequency, a special case exists at zero rate of flow where the received signal is not a valid Doppler flow signal, but rather purely noise. The noise at zero flow rate is random and will not have an average frequency which is unique to zero flow. Thus, the average frequency calculation algorithm would calculate an erroneous flow rate at zero flow based upon the average frequency received.

Although the noise at zero flow is random, it has been roughly characterized as consisting mainly of low amplitude white noise with occasional spikes of normal amplitude, low frequency noise. The terms low amplitude and low frequency are utilized when compared against a valid Doppler signal. If, however, this noise was interpreted as an actual Doppler signal, the average frequency of the white noise could correspond to flow rates typically of from 2.0 to 8.0 liters per minute, and the average frequency of the normal amplitude noise could correspond to flow rates typically of from 0.0–0.3 liters per minute.

Thus the Doppler blood flow system and method of the present must invoke a special case determination of when a zero flow condition exists in order to accurately provide a blood flow rate. Thus the present invention provides a method of determining the rate of flow of a fluid containing particles flowing through a tube. An ultrasonic signal is transmitted through the tube at an oblique angle thereto. The ultrasonic signal which has been reflected off of the particles contained in the fluid is received as a received ultrasonic signal. The rate of flow of the fluid is calculated from the received ultrasonic signal using Doppler techniques. Whether the special case of the value of the rate of flow being equal to zero exists is determined and the value of the rate of flow is set equal to zero for the special case.

In one embodiment of the invention the determining step includes measuring the magnitude of the amplitude of the received ultrasonic signal, comparing the magnitude of the received ultrasonic signal with a predetermined magnitude value and deciding that the special case of the value of the rate of flow being equal to zero exists when the magnitude of the received ultrasonic signal does not exceed the predetermined magnitude value.

In another embodiment of the invention the determining step includes measuring the rate of flow of the received ultrasonic signal for a plurality of sample times, counting the number of the sample times in which the rate of flow does not exceed a predetermined value and deciding that the special case of the value of the rate of flow being equal to zero exists when the number of the sample times in which the rate of flow does not exceed the predetermined value exceeds a predetermined portion of the plurality of sample times.

The present invention also provides an apparatus for determining the rate of flow of a fluid containing particles flowing through a tube. A transmitting mechanism is provided for transmitting an ultrasonic signal through the tube at an oblique angle thereto. A receiving mechanism receives the ultrasonic signal which has been reflected off of the particles contained in the fluid creating a received ultrasonic signal. A calculating mechanism calculates the rate of flow of the fluid from the received ultrasonic signal using Doppler techniques. A determining mechanism determines whether the special case of the value of the rate of flow being equal to zero exists and setting the value of the rate of flow equal to zero for the special case.

In one embodiment of the invention the determining mechanism includes measuring the magnitude of the amplitude of the received ultrasonic signal, compares the magnitude of the amplitude of the received ultrasonic signal with a predetermined magnitude value and decides that the special case of the value of the rate of flow being equal to zero exists when the magnitude of the received ultrasonic signal does not exceed the predetermined magnitude value.

In another embodiment of the invention the determining mechanism measures the rate of flow based upon the received ultrasonic signal for a plurality of sample times, counts the number of the sample times in which the rate of flow does not exceed a predetermined magnitude value and decides that the special case of the value of the rate of flow being equal to zero exists when the number of the sample times in which the rate of flow does not exceed the predetermined value exceeds a predetermined portion of the plurality of sample times.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Modern digital blood flowmeters rely on the well known Doppler effect to make accurate measurements on the flow of blood in a tube, or conduit, external to the patient. The Doppler technique relies on the interaction between a series in incident sound waves and moving particles in the blood. A common example of the Doppler effect is drop in pitch of a car horn as you pass a car moving in the opposite direction. In its most basic form, the Doppler principle states that if a receiver moves relative to the source then the frequency of the sound as seen by the receiver is not the same as the frequency sent out by the source. If the receiver moves toward the source then the frequency is shifted up, and if the receiver moves away from the source then the frequency is shifted down.

In the case of a blood flowmeter, both the source and the receiver are stationary, while the sound is reflected off of a moving target (particles in the blood). The moving target then acts as the moving source transmitting at a shifted frequency from the original source. The receiver then picks up the reflected signal having been shifted in frequency.

Human blood is composed of a liquid called plasma, red blood cells, white blood cells and platelets. The red blood cell is a biconcave disc with an average diameter of about 7 microns and an average thickness of about 2 microns. The mean volume of a red blood cell is about 90 cubic microns and there approximately 5,000,000,000 red blood cells per cubic millimeter of blood. This concentration corresponds to a haematocrit of about forty-five percent (45%). The number of white blood cells is relatively small, namely about 7,500. The platelets are much smaller than the red blood cells.

As the sound wave is reflected from the moving blood, the sound wave (signal) is generally scattered. Because the red blood cells are much larger than the platelets and much more numerous than the white blood cells, they are the major cause of scattering in the reflected sound wave (signal). This scattering is a random process. This random process obeys the Rayleigh scattering law, namely that if the particle size is much less than the wavelength of the incident wave (in this case $7 \times 10^{-6}$ meters particle size versus a wavelength in blood of $3.75 \times 10^{-4}$ meters for a 4 megaHertz ultrasound source the particle becomes a point source). The wavelength of the ultrasound signal is about 100 times larger than the red blood cell, therefore the red blood cell acts as a point scatter to the incident sound wave. Further, the scattering process will be governed by the Poisson probability distribution.

Figure 1:
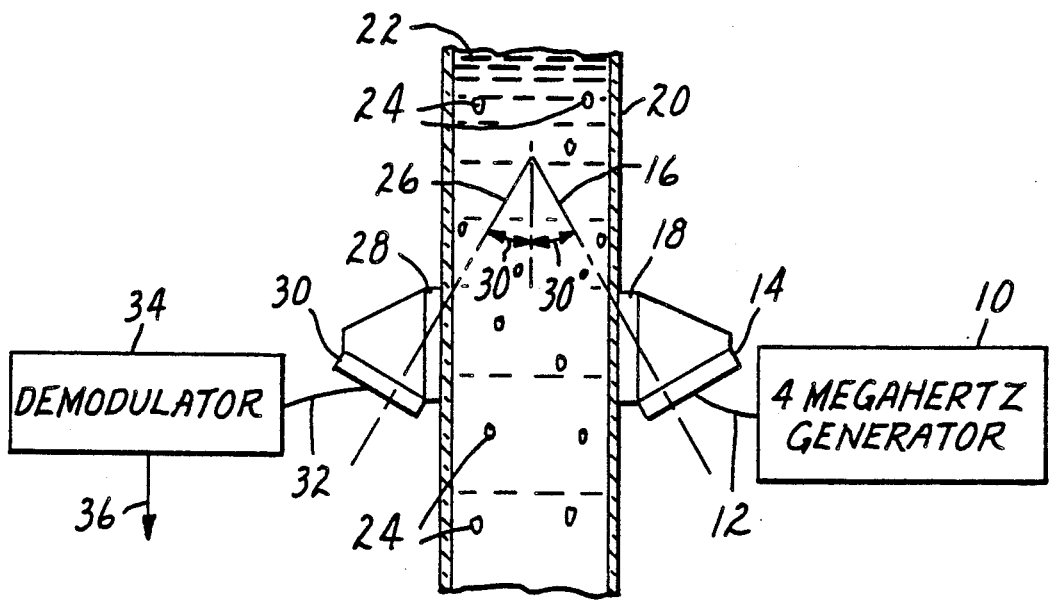
FIG. 1 is an illustration of the ultrasonic transmission and reception portion of the Doppler blood flow system of the present invention (portions of which are shown in section for clarity)

As can be seen by reference to FIG. 1, the source 10, an oscillator or a 4 megaHertz signal generator, produces a 4 megaHertz sinusoidal waveform 12 which is applied to a piezoelectric crystal 14 which produces a 4 megaHertz ultrasonic wave 16. This ultrasonic wave 16 is transmitted through an acrylic "lens" 18 to the surface of tubing 20, or conduit, containing the flowing blood 22. The "lens" 18 allows the attachment of the piezoelectric crystal 14 to the wall of tubing 20 so that the ultrasonic wave 16 makes an oblique angle with the flowing blood 22. Preferably this angle is approximately thirty degrees (30°). The ultrasonic wave 16 then enters the blood 22 through the wall of the tubing 20. The red blood cells 24 in the blood 22 then reflect and backscatter the ultrasonic wave 16 (transmitted signal). These red blood cells 24 act as small "transmitters", transmitting a reflected ultrasonic wave 26 which has been shifted in frequency. Some of the reflected or backscattered wave 26 passes back through the wall of tubing 20, through another acrylic "lens" 28 to another piezoelectric crystal 30 which converts the reflected ultrasonic wave 26 into an electric signal 32. "Lens" 28 also allows the attachment of piezoelectric crystal 30 to the wall of tubing 20 at an oblique angle thereto. Preferably this angle is equal to the angle made by "lens" 18, and preferably is approximately thirty degrees (30°). The frequency of the signal 32 at this point consists of the original 4 megaHertz ultrasonic signal 12 plus (or minus) the frequency shift due to the Doppler effect. Signal 32 is then passed to demodulator 34 which separates the portion of the signal 32 containing the frequency shift from the original 4 megaHertz transmitted signal 12. Thus the output 36 of demodulator 34 consists only of the frequency shift due to moving flow of blood 22 through tubing 20.

The parts illustrated in FIG. 1, including the generator 10, piezoelectric crystal 14, lens 18, tubing 20, lens 28, piezoelectric crystal 30 and demodulator 34 are well known in the art. These parts are identical in a Doppler flowmeter using analog signal processing techniques marketed by the Sarns, Inc. subsidiary of Minnesota Mining and Manufacturing Company, the assignee of the present invention, under Model No. 7800. The system described in U.S. Pat. No. 4,690,002, Hubbard et al, also assigned to Minnesota Mining and Manufacturing Company, also discloses an ultrasonic Doppler blood flow measurement system utilizing the components described in FIG. 1, and is hereby incorporated by reference.

The received and demodulated signal 36 has been "Doppler shifted" and the average frequency of this signal is linearly related to rate of flow of blood 22 in tubing 20. In the preferred flowmeter system, the average frequencies range from 0 to 5 kiloHertz which correspond to flow rates of from 0 to 8 liters per minute (LPM).

Theoretically, the received and demodulated signal 36 would be a single frequency representing the rate of flow of the blood 22. This single frequency result can only be achieved if several restrictions are met. An infinitely wide plane target must move at constant velocity through a monochromatic ultrasonic field which has an infinite beam width and if all targets were moving at the same velocity. In practice, of course, this does not occur. The result in practice is a signal which over time produces components of varying amplitude and varying frequency. As a result the signal 36 containing the Doppler information must be further processed in order to properly extract the frequency information indicative of the rate of blood flow.

Figure 2:
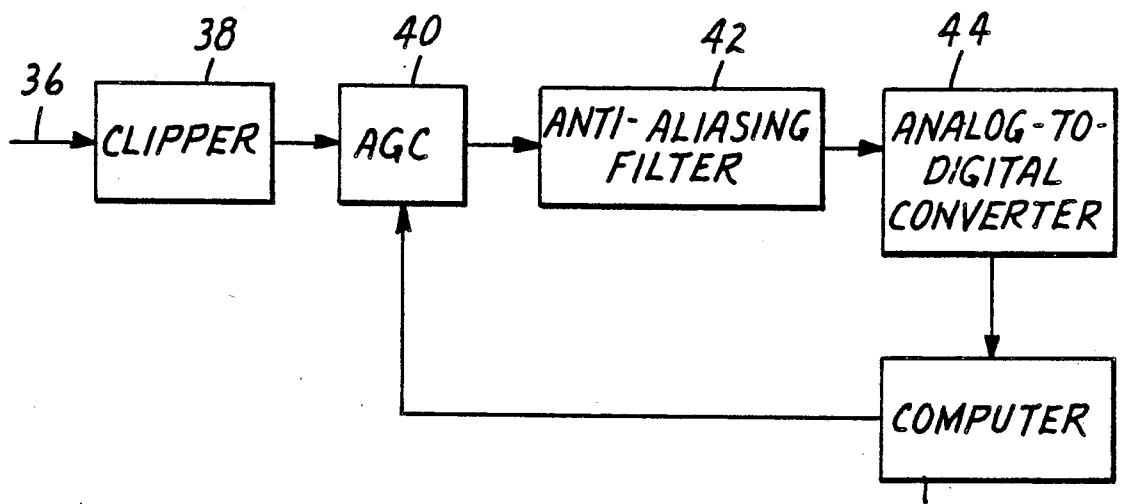
FIG. 2 is a block diagram of the signal processing portion of the Doppler blood flow system of the present invention.

This processing occurs in the circuitry illustrated in FIG. 2. The Doppler output signal 36 from FIG. 1 is supplied to a clipping circuit 38, preferably a diode clipping circuit. Since the blood 22 may contain air bubbles or significant concentrations of red blood cells 24 which would produce a reflected wave 26 and subsequent Doppler output signal 36 which would be of significantly increased magnitude. In order to limit the Doppler output signal 36 so that subsequent circuitry may properly process it, the signal 36 is clipped by clipping circuit 38 to limit its maximum amplitude. Clipping circuit 38 is conventional in nature and is also contained in the Sarns Model No. 7800 flowmeter.

The clipped signal is then supplied to AGC circuit 40 which provides automatic gain control. The AGC circuit 40 is preferably a SC11310CN by Sierra Semiconductor. AGC circuits are conventional in Doppler systems in order to provide automatic gain control of the signal to be processed. Conventional automatic gain control circuits operate by sensing the amplitude of the received signal and adjusting their gain accordingly. As will be seen in the subsequent description, AGC circuit 40 operates under software control. That is, the software determines the gain which the AGC circuit 40 provides. While this is the preferred embodiment of AGC circuit 40, it is within the contemplation of the present invention that a conventional real-time amplitude controlled AGC 40 circuit could be utilized.

The signal is then supplied to an anti-aliasing filter 42 and is digitized by analog-to-digital converter 44 which includes a sample and hold circuit. Anti-aliasing filters in connection with Doppler systems are conventional in nature and well known in the art. It is preferred that anti-aliasing filter 42 be a HSCF24040ACJ by Honeywell. This circuit allows the characteristics of the filter to be set under software control according to well known and conventional criteria. Although preferred it is within the contemplation of the present invention that a conventional non-software controlled anti-aliasing filter could be utilized. The preferred analog-to-digital converter 44 is a CSZ5112-KJ12 by Crystal Semiconductor. This analog-to-digital converter 44 is a 12-bit converter which gathers data samples at a rate of 41.67 kiloHertz. Again A-to-D converters are conventional in Doppler systems and any of a variety of A-to-D converter circuits could be employed here.

Once the Doppler signal has been converted to digital format in analog-to-digital converter 44, the signal may be processed digitally by computer 46. The preferred computer 46 includes a model TMS320C25 16-bit digital signal processor by Texas Instruments. The purpose of computer 46 is to extract the frequency information from the digital Doppler signal so that the rate of blood flow may be determined. While generally the use of a computer 46 to extract the rate of blood flow information from the digital Doppler is well known in the art, the particular routines utilized in the methods and apparatus of the present make the information extracted particularly accurate and useful. It is the particular subroutines utilized in the digital signal processing which is the essence of the present invention. The general ability to convert the digital Doppler signal to a rate of blood flow is known.

While the digital Doppler signal contains the information relating to the rate of flow of blood 22 through tubing 20, the digital Doppler signal also contains other information, particularly noise which make the analysis of the digital Doppler particularly difficult. The goal of the present flowmeter system and method is to calculate flow rates with a ± ten percent (10%) accuracy from 0.7 to 7.0 liters per minute. To allow interchangeability of probes (the Doppler transmitting and receiving hardware described in FIG. 1) the calculation software allows for the receipt of "probe characterization numbers" to calibrate the calculations for individual probes, as the relationship between average frequency and flow rate may be different for different probes.

Figure 3:
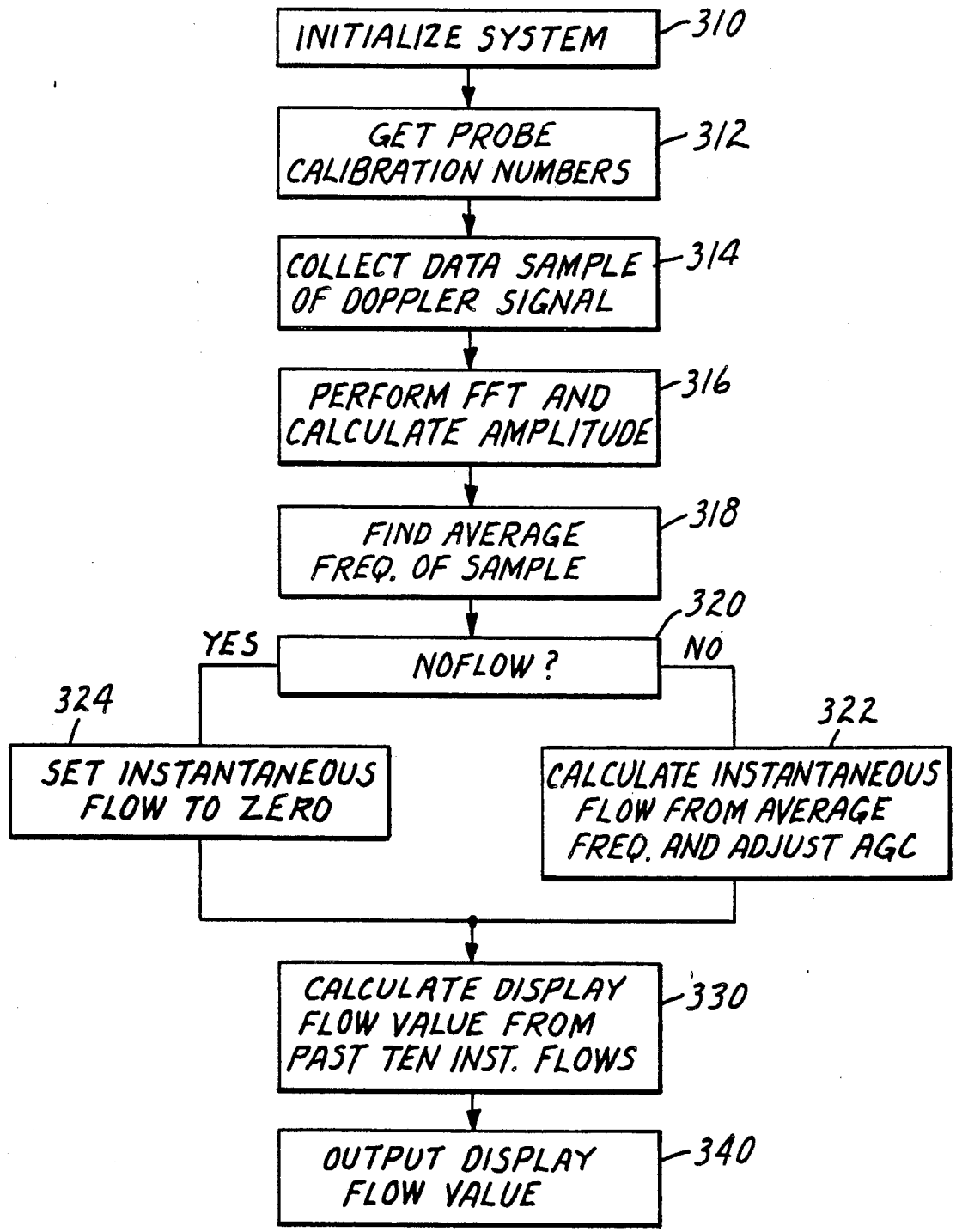
FIG. 3 is a flow chart of the main software algorithm associated with the apparatus and method of the present invention.

The basic algorithm performed by the software of computer 46 is illustrated in FIG. 3. The software gathers the digital samples of the digitized Doppler signal, calculates the average frequency of the signal and then converts this frequency to a flow rate based upon a known, linear relationship between average frequency and the rate of flow. The software also performs averaging of past data samples to determine an accurate and stable flow reading and, as will be seen below, includes steps to determine if the special case of zero flow exists. The preferred software embodiment of this main program loop is shown in Attachment A.

After initialization 310, which simply involves preparation of look-up tables according to well known techniques, the main loop of the program begins and is performed continuously until the computer 46 is reset. The preferred software embodiment of the initialization step 310 is shown in Attachments B and C. First the "probe characterization number" is read 312 to adjust the calculations to the particular probe being utilized. The preferred embodiment of receiving the probe characterization numbers is shown in Attachment D. The digital waveform is then obtained 314 by collecting a 1024 point sample of the incoming Doppler signal from the analog-to-digital converter 44. The waveform is then converted 316 into the frequency domain by Fast Fourier Transform (FFT) to calculate the frequency distribution of the signal. The preferred embodiment of the data sampling and FFT calculation steps is shown in Attachment E. In addition, the actual amplitude of the incoming signal is also calculated from the 1024 data points and stored in a table containing the amplitudes of the past 10 samples. This amplitude data is utilized later in a special subroutine related to zero flow detection. Next, the average frequency of the Doppler signal is calculated 318 from the FFT results (this calculation subroutine is described later in reference to FIG. 6). Unless a zero flow condition exists 320, which will be described in conjunction with FIG. 7, the instantaneous flow rate is calculated 322 based upon the average frequency of the sample and the probe characterization numbers. If a zero flow condition exists, then the instantaneous flow rate is set 324 to zero.

The instantaneous flow rate calculation 322 is calculated by first subtracting the intercept value from the average frequency and then dividing the result by the slope value.

In addition to calculating 322 the instantaneous flow rate, the power level of the incoming signal is analyzed and, based upon the power level of the incoming signal, a new gain value is supplied to the AGC circuit 40. The maximum and minimum voltages which can be measured by the preferred analog-to-digital converter 44 are ±2.5 volts. The AGC circuit 40 can be software controlled by being sent an integer between 0 and 255 (8-bits) corresponding to a gain or loss of 0 to 25.5 dB. The ninth bit of data indicates whether gain or loss is desired. The automatic gain is controlled by measuring the average absolute value amplitude of the sampled signal to a constant which represents the target signal strength. If the measured signal is less than the target, the gain is increased by 0.5 dB and if the measured signal is greater than the target, the gain is decreased by 0.5 dB. The 0.5 dB increase or decrease in gain corresponds to an increase or decrease of 5 in the integer value sent to the AGC circuit 40 be the software. The probe characterization numbers used in this calculation represent the slope and intercept values of a plot of average frequency versus flow rate for a particular probe. They are predetermined in manufacture by measuring the average frequency at various flow rates for each individual probe, and then performing a least square linear fit on the data.

The instantaneous flow rate is averaged 330 over the past ten instantaneous flow rates. If the averaged flow rate then differs by more than 0.1 liters per minute then the display (or output) may be updated. Otherwise the display (or output) is not updated to prevent needless "toggling" of the output data. This averaged flow rate (display flow rate) may be displayed 340 or otherwise utilized.

Figure 4:
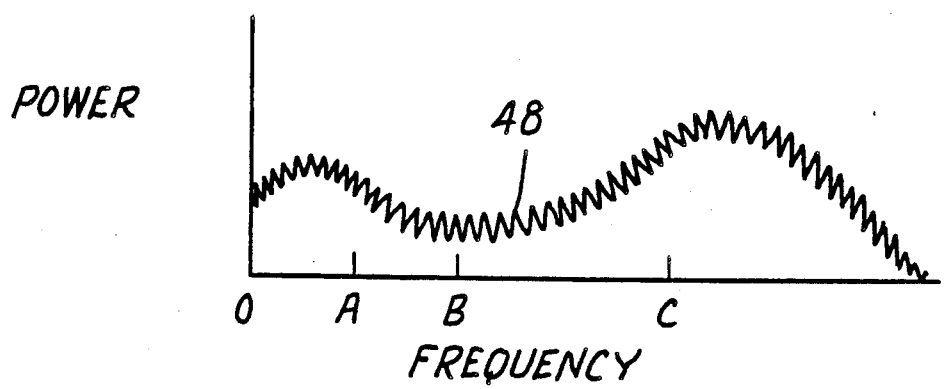
FIG. 4 is a graph of an exemplary raw Doppler signal.

In order to properly determine the rate flow of the blood 22 flowing in tubing 20, a proper analysis of the characteristics of the incoming Doppler signal must be made. FIG. 4 illustrates a typical Doppler signal 48 in the frequency domain. The chart of FIG. 4 is a plot of the Doppler signal with frequency as the horizontal axis and amplitude (or power) as the vertical axis. As can be seen the signal 48 is not a single frequency representing the flow rate but because of a number of reasons including those discussed above relating finite wave width and particle size signal 48 is really an entire range of frequencies in which certain frequencies predominate (illustrated by increased magnitude of the signal or "humps"). Signal 48 has actually two "humps", one at a higher frequency which represents the actual information bearing content of the signal related to flow rate and one at a lower frequency which is caused by motor noise from the blood pump (not shown) or other vibrations. Since the flow rate is related to average frequency of the information bearing portion of the signal 48, to take the actual average frequency of signal 48 would result in frequency C in FIG. 4. Since this average frequency is influenced by the low frequency "hump" caused by motor or pump noise, an inaccurate result is obtained.

Figure 5:
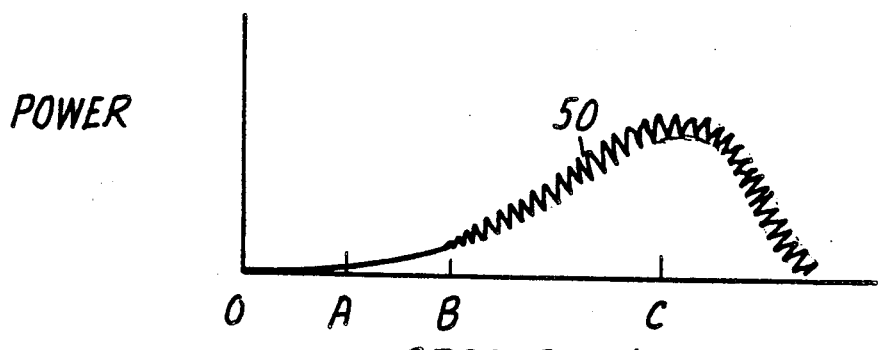
FIG. 5 is a graph of the exemplary Doppler signal of FIG. 4 having been processed according to one of the aspects of the present invention.

In order to eliminate the low frequency "hump" in FIG. 4, the software calculates the average frequency of signal 48 and then divides that average frequency by 4 to obtain frequency A in FIG. 4. In general the low frequency "hump" noise is contained within the range from zero to frequency A. The software then makes a piece-wise exponential estimation of the Doppler signal ignoring the low frequency "hump" below frequency A. In order smooth the Doppler signal in the low frequency range the curve is estimated and smoothed between the frequency range of zero and the average frequency (Frequency C) divided by 2 (Frequency B). The result of this software elimination of the low frequency noise "hump" is shown by the modified signal 50 illustrated in FIG. 5.

Figure 6:
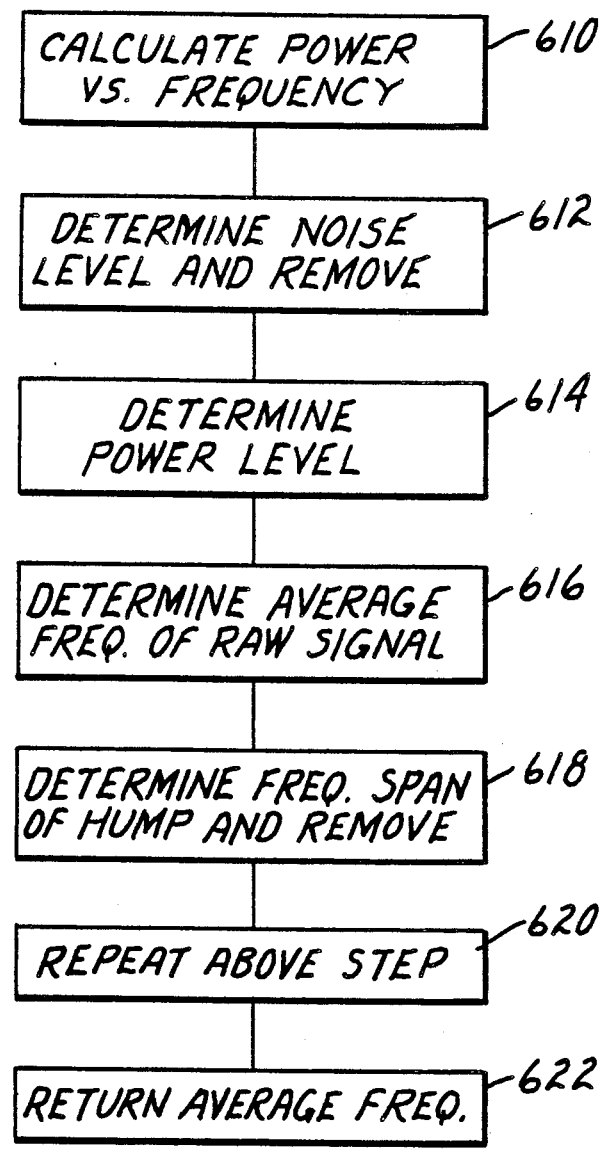
FIG. 6 is a flow chart of a portion of the software algorithm associated with the determination of the average frequency of the Doppler signal according to one aspect of the present invention.

FIG. 6 illustrates a flow chart of portion of the software which calculates the average frequency (block 318 of FIG. 3). The power vs. frequency is calculated in block 610 as shown in Attachment F. The sum of the power at each frequency is multiplied by the frequency. The result of this multiplication is then divided by the sum of the power at each frequency. All frequency values are linearly normalized such that integers 0-255 represent frequencies 0-10 kiloHertz. The actual average frequency is found by multiplying the normalized average frequency by 40.77 at the end the algorithm.

In addition to the average frequency calculation, this portion of the software performs the signal processing which eliminates the low frequency hump noise discussed. above. It has been found that normal Doppler signals contain two specific types of noise which must be eliminated to be able to calculate an accurate rate of flow. The first type of noise is a base line white noise with a bandwidth much larger than any valid Doppler signal. Because it has been shown experimentally that valid Doppler frequencies in the preferred flowmeter system are limited to 0-9 kiloHertz, the software eliminates this base line noise by finding the largest power value between 9 and 10 kiloHertz (above the expected information containing portion of the Doppler signal) and subtracting 612 this value from every input data value of the Doppler signal. The second type of noise is caused by vibrations within the physical sensor/tubing/blood system and is the low frequency hump noise discussed above. This noise appears as a hump which exists over a range of frequencies much lower than the main frequency hump associated with the valid rate of flow data. To eliminate this low frequency hump, first the power spectrum of the signal is determined 614. Next, the average frequency of the raw signal (including the low frequency hump) is determined 616. Next the average power level between the range average frequency/4 (Point A in FIG. 4) and average frequency/2 (Point B in FIG. 4) is determined. Next, the power data values from zero to average frequency/2 are replaced by an exponentially increasing function from zero at zero Hertz to the calculated value of power at the frequency of the average frequency/2 (block 618). A new average frequency value is then calculated from the corrected power distribution data. To eliminate any gross errors caused by a large low frequency hump in the initial calculation, the hump removal process is repeated 620 once. The average frequency value is then returned to the main program 622. The preferred software embodiment of the find average frequency algorithm is shown in Attachment F.

Because the flowmeter of the present invention and the method invoked therein calculates flow rate solely on the basis of frequency, a special case exists at zero rate of flow where the received signal is not a valid Doppler flow signal, but rather purely noise. The noise at zero flow rate is random and will not have an average frequency which is unique to zero flow. Thus, the average frequency calculation algorithm would calculate an erroneous flow rate at zero flow based upon the average frequency received. Although the noise at zero flow is random, it has been roughly characterized as consisting mainly of low amplitude white noise with occasional spikes of normal amplitude, low frequency noise. The terms low amplitude and low frequency are utilized when compared against a valid Doppler signal. If, however, this noise was interpreted as an actual Doppler signal, the average frequency of the white noise could correspond to flow rates typically of from 2.0 to 8.0 liters per minute. The low frequency normal amplitude noise corresponds to flow rates of 0.0-0.3 liters per minute.

Figure 7:
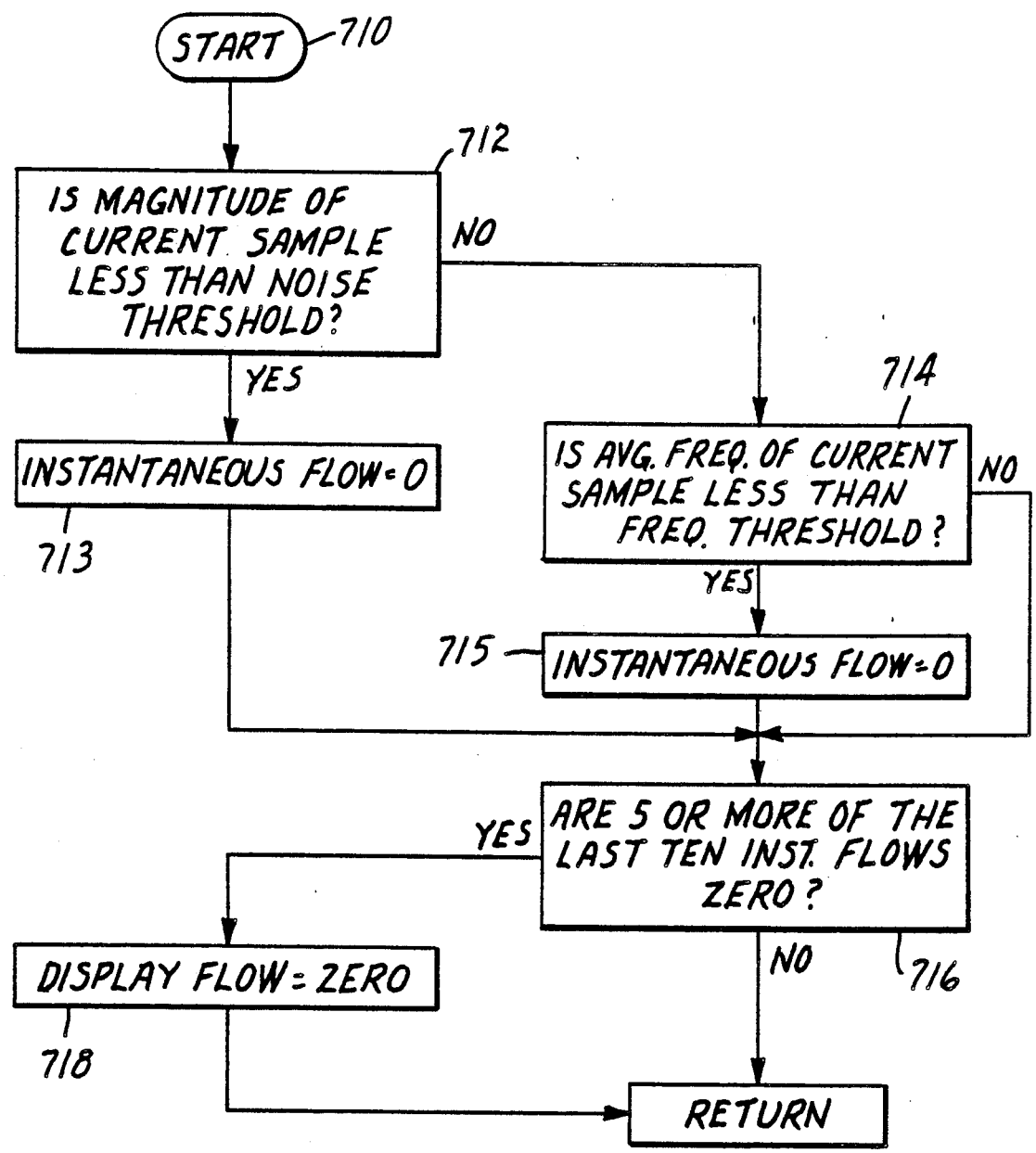
FIG. 7 is a flow chart of a portion of the software algorithm associated with the determination of the special zero flow case according to one aspect of the present invention.

Thus, the software preferred embodiment utilized three steps to ensure the start of detection 710 of zero flow as illustrated in FIG. 7. First, the average amplitude of the incoming signal is determined (see block 314 of FIG. 3) and is compared 712 to a predetermined noise threshold. If the current amplitude is below this value (see block 324) then the instantaneous flow rate is set 713 to zero, ignoring the average frequency of the incoming signal. Correct action of this step requires that a safe and predictable margin exists between the amplitude of the zero flow signal and the amplitude of a valid Doppler signal. Second, the instantaneous flow rate is set 715 to zero for all instantaneous flow rates which are less than 0.4 liters per minute (714), i.e., 0.3 liters per minute or less. By doing this, the software ensures that the occasional spikes of low frequency noise will not appear as valid flow readings. Third, the last ten instantaneous flow rates are examined 716, and if a majority of the values are zero, then a zero flow rate is determined to exist 718. Without this third step it would be possible for two or three non-zero instantaneous flow at zero flow to cause an erroneous non-zero flow rate determination as the flow rate otherwise is calculated by averaging the instantaneous flows.

Thus, it can be seen that there has been shown and described a novel Doppler blood flow system and method therefore. It is to be recognized and understood, however, that various changes, modifications and substitutions in the form and the details of the present invention may be made by those skilled in the art without departing from the scope of the invention as defined by the following claims.

---

ATTACHMENT B

BEGIN
1     Download program from EPROM to SRAM
2     Wait for initial AtoD interrupt
3     Write to BOOT port to begin program execution out of SRAM
4     Branch to main program
END of start-up/reset sequence

---

ATTACHMENT A

BEGIN
0    Perform start-up/reset sequence copying program from EPROM to SRAM
1    Initialize hardware devices(timer chip, programmable gain loss chip (PGLC),programmable anti-aliasing filter, and the RS232 communications port)
2    Initialize algorithm variables (main loop counter and look-up tables)
3    Get probe characterization numbers from the switch board interface and determine if valid
4    Do forever {Main Loop}
     4.1   Every 31 times through the loop, read the characterization numbers from the switch board
     4.2   Sample the received signal and calculate frequency distribution
         4.2.1   Collect 1024 data points from the AtoD converter
         4.2.2   Calculate the average absolute amplitude of the data sample (after the PGLC)
         4.2.3   Perform Fast Fourier Transform(FFT) on the data sample
         4.2.3   Combine the real and imaginary results of FFT to get the power vs. frequency distribution of the data sample
     4.3   Calculate the amplitude of the signal before the PGLC and update the array containing the amplitude levels of the past ten samples {to be used to determine if zero flow exists}
     4.4   Find the average frequency of the data sample from the power vs frequency information
     4.5   If the amplitude value of the last sample is less than the noise threshold then
         4.5.1   Set the instantaneous flow rate to zero
     4.6   Else
         4.6.1   Calculate the instantaneous flow rate from the average frequency of the sample and the probe characterization numbers
         4.6.2   Set the gain of the PGLC (to limit signal amplitude at filter and AtoD inputs)
     4.7   Calculate the display flow value based on the previous ten instantaneous flow rates.
     4.8   Output the display flow value
End of Do loop
END of main program algorithm

---

ATTACHMENT C

BEGIN
1    Initialize the data aray Freq to contain the floating point notation of integers between 0–256, which will be used as the normalized frequencies representing actual frequency values between 0–10 kHz.
2    Initialize data array Factor. This array contains the floating point notation of the actual v/v gain of the PGLC for values of programmed gain from 0 to 255 in increments of 5.
3    Initialize PGLC for no gain.
4    Initialize switched capacitor filter chip for the following:
       RCF Bandage = 14kHz
       DC Gain = 1 v/v
       Clock to SCF Bandedge Ratio = 400 (0.1dB Bandwidth of SC filter = 10kHz)
       Decimator Sample Rate = 4.167 (Sample rate = 41.67kHz)
5    Initialize the timer chip for:
       Counter 0 (AtoD hold ~ generation) = one shot mode, with a count = 4
       Counter 1 (Flow Rate output) = intialized in one shot mode which disables the output (setting initial flow rate = 0).
       Counter 2 (Baud Rate generation) = square wave mode, with count = 3333 to set-up 1200Hz baud rate.
6    Initialize USART for RS232 communication with 8 data bits, 2 stop bits, no parity, and 1200 baud rate.
END of initialization

---

ATTACHMENT D

BEGIN
1    Read the 8 digits from the switch board
     1.1 For each of the 8 switches
         -write to the appropriate switch port to begin read cycle - this wll enable the switchsel~ and the appropriate switch address lines.
         -wait approximately $10 \times 10^{-6}$ sec
         -read the switch value from the appropriate switch port
     1.2   Write to I/O port7 to deassert switchel~ cycle.
2    Calculate checksum = (sum of digits 0–2, 4–7) modulo 10

ATTACHMENT D

3 If checksum = switch 3 value then
   7.3.1 Calculate slope = digit 0 + (digit 1*10) + (digit 2 * 100)
   7.3.2 Calculate intercept = digit 4 + (digit 5*10) + (digit 6 * 100)
4 If (checksum<>digit 3) or (calculated slope and intercept numbers) are outside of the
  expected range of values then set slope and intercept to default values and set probe number validity
  to false.
END of reading probe characterization numbers from the switch board

ATTACHMENT E

BEGIN
1 Collect 1024 digital data points from the AtoD converter
  1.1 Enable interrupts
  1.2 Wait for an interrupt
  1.3 Read a 16 bit data value from the AtoD, −2.5 volts = 0000 2.5 volts = FFFF
    (bottom 4 bits are filled with zero by the 12 bit AtoD)
  1.4 Convert data to center values at 0,0 volts = 0000
    1.4.1 Shift data right to eliminate sign bit −2.5 v = 0000 2.5 v = 7FFF
    1.4.2 Subtract 3FFF to center values at zero, −2.5v = C001 (−3FFF) 2.5v = 3FFF
  1.5 Place the data value in an array followed by a data point of zero to represent the complex value
    of the data sample. (The input to the FFT must be an array of 1024 complex points.)
  1.6 Repeat steps 1.2–1.4 for 1023 additional points
2 Calculate the average absolute amplitude of the sample
  2.1 Set the variable total to 0
  2.2 Add the absolute value of each data point total
  2.3 Set the average absolute amplitude to total/1024
3 Perform the 1024 complex point FFT. The FFT algorithm and code was adapted from information in
  Texas Instrument's Digital Signal Processing Applications with the TMS320 Family, pages 69–
  170, and is 1024 point, radix 2 differential FFT algorithm. The result of the FFT is 1024 complex
  points, of which the first 256 represent amplitude values at discrete frequencies from 0 to 10kHz.
4 Convert the complex FFT output to a power distribution array.
  4.1 For each of the first 256 complex points
    4.1.1 Square the real and imaginary components
    4.1.2 Added the squared components together
    4.1.3 Store the result in an array of 256 values representing the power versus frequency
       distribution of the 1024 point sample
END of data gathering and FFT calculation

ATTACHMENT F

BEGIN
1 Determine the noise threshold level and subtract it from all power values
  1.1 Find the maximum power value between 9 and 10 kHz
  1.2 Subtract the maximum power value from all power values in the input array; if any values are
    less than zero, set to them zero
2 Determine the normalized average frequency of the sample
  2.1 Calculate the normalized average frequency of the unmodified data
    2.1.1 Set power_w_sum, power_sum to 0
    2.1.2 For i = 1 to 256 do
        power_w_sum = power_w_sum + (FFTData(i) * Freq(i))
        power_sum = sum = power_sum + FFTData(i)
    2.1.3 average frequency = power_w_sum/power_sum
  2.2 Determine normalized frequency span of low frequency hump and eliminate
    2.2.1 Determine avg_power between [avg_freq/2]and [avg_freq/4]
    2.2.2 Set power values from zero to [avg_freq/2] so that they exponentially increase from
       zero at 0 Hz to a power level equal to [avg_power/2] at [avg_freq/2].
    2.2.3 Recalculate the normalized average frequency (same as step 2.1)
  2.3 Repeat step 2.2 to eliminate any gross error in the initial calculation of the normalized average
    frequency caused by a large low frequency hump.
3 Multiply the normalized average frequency by 40.77 to result in the actual average frequency, in the
  range of 0 to 10 kHz.
END of average frequency calculation

What is claimed is:

1. A method of determining a value of rate of flow of a fluid containing particles flowing through a tube, including a determination of whether a special case of the value of said rate of flow being equal to zero exists, comprising the steps of:

transmitting an ultrasonic signal through said tube at an oblique angle thereto;

receiving said ultrasonic signal which has been reflected off of said particles contained in said fluid creating a received ultrasonic signal which has an amplitude;

calculating a preliminary rate of flow of said fluid from said received ultrasonic signal using Doppler techniques, said preliminary rate of flow being said rate of flow unless said special case of the value of said rate of flow being equal to zero exists;

measuring the magnitude of the amplitude of said received ultrasonic signal with a predetermined magnitude value; and deciding that said special case of the value of said rate of flow being equal to zero exists when said magnitude of the amplitude of said received ultrasonic signal does not exceed said predetermined magnitude value.

2. A method of determining a value of rate of flow of a fluid containing particles flowing through a tube, including a determination of whether a special case of the value of said rate of flow being equal to zero exists, comprising the steps of:

transmitting an ultrasonic signal through said tube at an oblique angle thereto;

receiving said ultrasonic signal which has been reflected off of said particles contained in said fluid creating a received ultrasonic signal;

calculating a preliminary rate of flow of said fluid from said received ultrasonic signal using Doppler techniques, said preliminary rate of flow being said rate of flow unless said special case of the value of said rate of flow being equal to zero exists;

measuring the magnitude of said received ultrasonic signal with a predetermined magnitude value; and deciding that said special case of the value of said rate of flow being equal to zero exists when said magnitude of said received ultrasonic signal does not exceed said predetermined magnitude value.

3. An apparatus for determining a value of rate of flow of a fluid containing particles flowing through a tube, including a determination of whether a special case of the value of said rate of flow being equal to zero exists, comprising:

transmitting means for transmitting an ultrasonic signal through said tube at an oblique angle thereto;

receiving for receiving said ultrasonic signal which has been reflected off of said particles contained in said fluid creating a received ultrasonic signal which has an amplitude;

calculating means for calculating a preliminary rate of flow of said fluid from said received ultrasonic signal using Doppler techniques, said preliminary rate of flow being said rate of flow unless said special case of the value of said rate of flow being equal to zero exists;

measuring means for measuring the magnitude of the amplitude of said received ultrasonic signal with a predetermined magnitude value;

comparing means responsive to said measuring means for comparing said magnitude of said amplitude of said received ultrasonic signal with a predetermined magnitude value; and deciding means responsive to said comparing means for deciding that said special case of the value of said rate of flow being equal to zero exists when said magnitude of the amplitude of said received ultrasonic signal does not exceed said predetermined magnitude value.

4. An apparatus for determining a value of rate of flow of a fluid containing particles flowing through a tube, including a determination of whether a special case of the value of said rate of flow being equal to zero exists, comprising:

transmitting means for transmitting an ultrasonic signal through said tube at an oblique angle thereto;

receiving for receiving said ultrasonic signal which has been reflected off of said particles contained in said fluid creating a received ultrasonic signal;

calculating means for calculating a preliminary rate of flow of said fluid from said received ultrasonic signal using Doppler techniques, said preliminary rate of flow being said rate of flow unless said special case of the value of said rate of flow being equal to zero exists;

measuring means for measuring the rate of flow based upon said received ultrasonic signal for a plurality of sample times;

counting means responsive to said measuring means for counting the number of said sample times in which said rate of flow does not exceed a predetermined value; and deciding means responsive to said counting means for deciding that said special case of the value of said rate of flow being equal to zero exists when said number of sample times in which said rate of flow does not exceed said predetermined value exceeds a predetermined portion of said plurality of sample times.

* * * * *

UNITED STATES PATENT AND TRADEMARK OFFICE
CERTIFICATE OF CORRECTION

PATENT NO. : 4,989,609

DATED : February 5, 1991

INVENTOR(S) : Dirk Robert Smith, et al

It is certified that error appears in the above-identified patent and that said Letters Patent is hereby corrected as shown below:

Column 5, line 57, "blood 22 through" should read --blood 22 flowing through--.

Signed and Sealed this

Tenth Day of May, 1994

*Attest:*

BRUCE LEHMAN

*Attesting Officer*     *Commissioner of Patents and Trademarks*